United States Patent [19]

Hess

[11] Patent Number: 4,808,164

[45] Date of Patent: Feb. 28, 1989

[54] CATHETER FOR BALLOON ANGIOPLASTY

[75] Inventor: Robert Hess, Portola Valley, Calif.

[73] Assignee: Progressive Angioplasty Systems, Inc., Los Angeles, Calif.

[21] Appl. No.: 88,264

[22] Filed: Aug. 24, 1987

[51] Int. Cl.⁴ ...................... A61M 25/00; A61B 17/36
[52] U.S. Cl. .................................... 604/95; 128/303.1; 128/344; 128/657; 604/96; 604/170
[58] Field of Search ............... 128/303.1, 303.11, 305, 128/344, 348.1, 656–658, 772, 341, 343; 604/96–103, 95, 170, 280–282

[56]  References Cited

U.S. PATENT DOCUMENTS

| | | | |
|---|---|---|---|
| 3,435,824 | 4/1969 | Gamponia | 128/334 |
| 3,618,614 | 11/1971 | Flynn | 128/348 |
| 3,720,210 | 3/1973 | Diettrich | 128/214.4 |
| 3,757,768 | 9/1973 | Kline | 128/2 M |
| 3,871,358 | 3/1975 | Fukuda et al. | 128/2 M |
| 4,033,331 | 7/1977 | Guss et al. | 128/2 M |
| 4,276,874 | 7/1981 | Wolvek et al. | 128/1 D |
| 4,285,341 | 8/1981 | Pollack | 128/214 R |
| 4,301,797 | 11/1981 | Pollack | 128/214 R |
| 4,323,071 | 4/1982 | Simpson et al. | 128/343 |
| 4,351,341 | 9/1982 | Goldberg et al. | 128/348 |
| 4,411,055 | 10/1983 | Simpson et al. | 29/447 |
| 4,445,892 | 5/1984 | Hussein et al. | 128/344 X |
| 4,448,188 | 5/1984 | Loeb | 128/303.1 X |
| 4,449,528 | 5/1984 | Auth et al. | 128/303.1 |
| 4,456,017 | 6/1984 | Miles | 128/772 |
| 4,538,622 | 9/1985 | Samson et al. | 128/772 |
| 4,545,390 | 10/1985 | Leary | 128/772 |
| 4,548,206 | 10/1985 | Osborne | 128/772 |
| 4,573,470 | 3/1986 | Samson et al. | 128/344 |
| 4,582,181 | 4/1986 | Samson | 128/348.1 |
| 4,616,653 | 10/1986 | Samson et al. | 128/344 |
| 4,619,274 | 10/1986 | Morrison | 128/657 X |
| 4,641,654 | 2/1987 | Samson et al. | 128/344 |
| 4,643,186 | 2/1987 | Rosen et al. | 128/303.1 |
| 4,654,024 | 3/1987 | Crittenden et al. | 128/303.1 X |
| 4,662,368 | 5/1987 | Hussein et al. | 128/303.1 |
| 4,669,465 | 6/1987 | Moore et al. | 128/303.1 |
| 4,672,961 | 6/1987 | Davies | 128/303.1 |
| 4,672,962 | 6/1987 | Hershenson | 128/303.1 |
| 4,676,249 | 6/1987 | Arenas et al. | 128/657 |
| 4,679,557 | 7/1987 | Opie et al. | 128/305 |
| 4,686,982 | 8/1987 | Nash | 128/305 |
| 4,719,924 | 1/1988 | Crittenden et al. | 128/657 X |
| 4,721,117 | 1/1988 | Mar et al. | 128/772 |
| 4,723,936 | 2/1988 | Buchbinder et al. | 128/344 X |
| 4,728,319 | 3/1988 | Masch | 128/305 X |
| 4,729,763 | 3/1988 | Henrie | 128/305 X |

FOREIGN PATENT DOCUMENTS 0176865 4/1986 European Pat. Off. .

Primary Examiner—Dalton L. Truluck
Attorney, Agent, or Firm—Burns, Doane, Swecker & Mathis

[57]  ABSTRACT

A catheter for balloon angioplasty includes a flexible shaft defining a hollow passage. The shaft has first and second ends. A core is movably and removably mounted in the passage and has first and second ends adjacent the first and second ends of the shaft. The core has a first flexible portion adjacent the first end and a second flexible portion of greater flexibility adjacent the second end. The core also has an enlarged terminal knob at the second end. A flexible guidewire may be fixed to the second end of one of the shaft and the core. The catheter may be inserted into a vascular tree and the core removed. The core may be replaced by an exchange wire, an angioscope, a laser fiber, or a rotatable bit. Also, when the core is replaced by an exchange wire, the shaft may then be removed and replaced by either a balloon angioplasty catheter or a perfusion catheter.

12 Claims, 3 Drawing Sheets

CATHETER FOR BALLOON ANGIOPLASTY

BACKGROUND OF THE INVENTION

This invention relates generally to surgical procedures using a flexible catheter guide and more particularly to an apparatus for use in balloon angioplasty.

BACKGROUND DESCRIPTION

Catheters require pushability and flexibility in order to be effectively inserted into blood vessels and maneuvered through a vascular tree. Often a hollow spring wire shaft is used and includes a movable core wire. A balloon may be used with the catheter so as to be expanded in the vessel and open blockages found therein. One such device relates to a balloon catheter which includes an elongated coil spring defining an inner passage. The spring has a silicone covering which includes an extendable sheath, strain collar, and a balloon tip affixed to the strain relief collar. A portion of the elongated coil spring and sheath form a support structure which perceptibly elongates when excessive stretching force is applied to the support structure in pulling the balloon through a body passage.

Another device relates to a coil spring guide with a deflectable tip which comprises a coil spring, a core wire within the coil spring extending the length of the coil spring, and a head member. The coil spring is covered with a sheath. A mechanism is provided at the proximal end of the coil spring guide for causing movement of the coil spring relative to the core wire. The core wire is eccentrically fixed to the back side of the head member and adjacent to a lateral side thereof. Thereby, rearward movement of the core wire causes compression of the distal end spring coils and deflection thereof in a direction laterally from the side of the head member to which the core extension is fixed. Standard low profile catheters with a fixed wire system do not offer, in addition, a combined over the wire system or variable column strength.

Still another device is directed to a catheter wire guide with a movable mandrel having a tapered tip which permits the flexibility of the distal tip of the wire guide to be varied. This device provides for "a helically wound wire having an opening therethrough. There is further provided a mandrel positioned within the opening and longitudinally movable therein relative to the helically wound wire for varying the flexibility of the distal tip of the wire guide."

Although the foregoing devices include some advantageous features, they are limited in that they do not combine the following desirable features: a movable core; variable stiffness of the shaft secondary to the moveable core; a deflection mechanism for deflecting the tip of the catheter while still allowing torque and rotation; ultra low-profile, such that it may be usable through a standard diagnostic coronary catheter rather than a guide catheter, referred to as a PTCA guiding catheter; ability to transform from a fixed wire system to an over-the-wire system by removing the movable core; and ability to insert either fiberoptic angioscopes or laser fibers, through the hollow portion of the catheter.

The foregoing illustrates limitations known to exist in present devices. Thus, it is apparent that it would be advantageous to provide an alternative directed to overcoming one or more of the limitations set forth above. Accordingly, a suitable alternative is provided including features more fully disclosed hereinafter.

SUMMARY OF THE INVENTION

In one aspect of the present invention, this is accomplished by providing a catheter for balloon angioplasty including a flexible shaft defining a hollow passage. The shaft has first and second ends. A core is movably and removably mounted in the passage and has first and second ends adjacent the first and second ends of the shaft. The core has a first flexible portion adjacent the first end and a second flexible portion of greater flexibility, adjacent the second end. The core also has an enlarged terminal knob at the second end. A flexible guidewire is optionally fixed to the second end of one of the shaft and the core.

The foregoing and other aspects will become apparent from the following detailed description of the invention when considered in conjunction with the accompanying drawing. It is to be expressly understood, however, that the drawing is not intended as a definition of the invention but is for the purpose of illustration only.

BRIEF DESCRIPTION OF THE DRAWING

FIG. 7 is a schematic view of a method of using the present invention.

DETAILED DESCRIPTION

Figure 1:
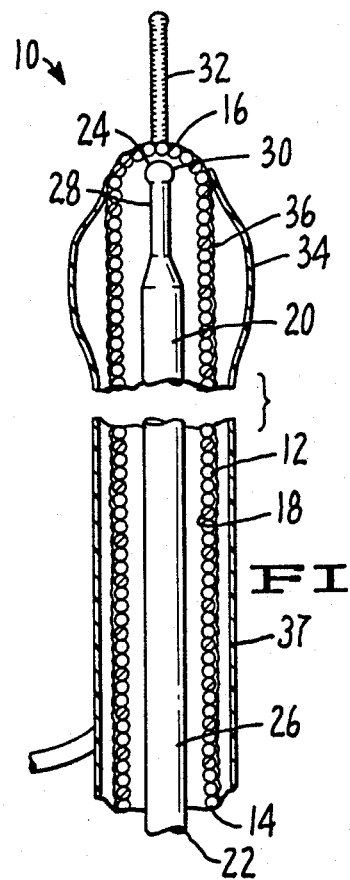
FIG. 1 is a diagrammatic view illustrating an embodiment of the catheter of this invention.

A catheter for balloon angioplasty is illustrated in FIG. 1 and is generally designated 10. Catheter 10 includes a flexible shaft 12 preferably formed of a suitable metal and having an outside diameter of from about 0.014 to about 0.035 inches. Shaft 12 has an open first or proximal end 14, a closed second or distal end 16 and defines a hollow passage 18 therein.

A flexible core 20 is preferably formed of a suitable metal and has a diameter of from about 0.010 to about 0.030 inches. Core 20 is movably and removably mounted within passage 18 and includes a first end 22 and a second end 24 adjacent first and second ends 14, 16, respectively of shaft 12. Core 20 has a first portion 26, adjacent first end 22, which has a first flexibility and a second portion 28, adjacent second end 24, which is tapered to a smaller diameter than first portion 26 to provide a second flexibility, greater than the aforesaid first flexibility. Core 20 also includes an enlarged terminal knob 30 formed at second end 24.

A flexible guidewire 32, preferably formed of a suitable metal and having an outside diameter of from about 0.008 to about 0.018 inches may be fixedly secured by suitable means such as adhesives welding or brazing, to second end 16 of shaft 12. Guidewire 32 is of a greater flexibility than the aforesaid second flexibility.

A inflatable member such as a well-known balloon 34 is attached or affixed to second end 16 of shaft 12 to substantially cover an external surface 36 of shaft 12 in such a manner that second end 16 of shaft 12 and guidewire 32 are free of such covering. A suitable means 38, see FIG. 2, may be connected via conduit 40 for inflating balloon 34. A finger loop 42 is suitably connected to shaft 12 and a corresponding finger loop 44 is similarly connected to core 20.

Figure 5:
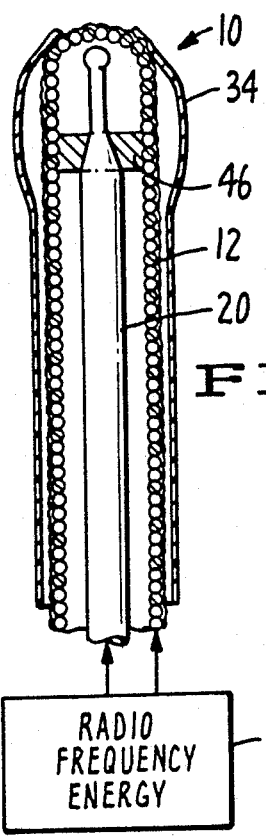
FIG. 5 is a diagrammatic view illustrating a further embodiment of this invention.
Figure 6:
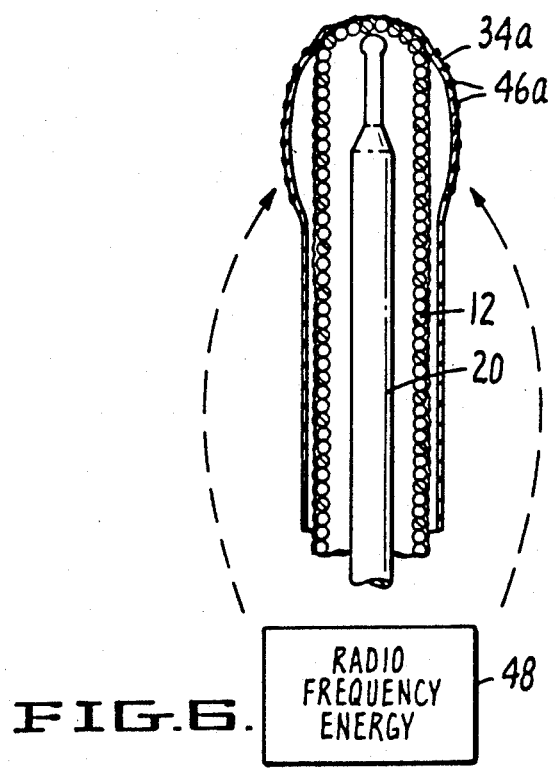
FIG. 6 is a diagrammatic view illustrating a still further embodiment of this invention.
Figure 2:
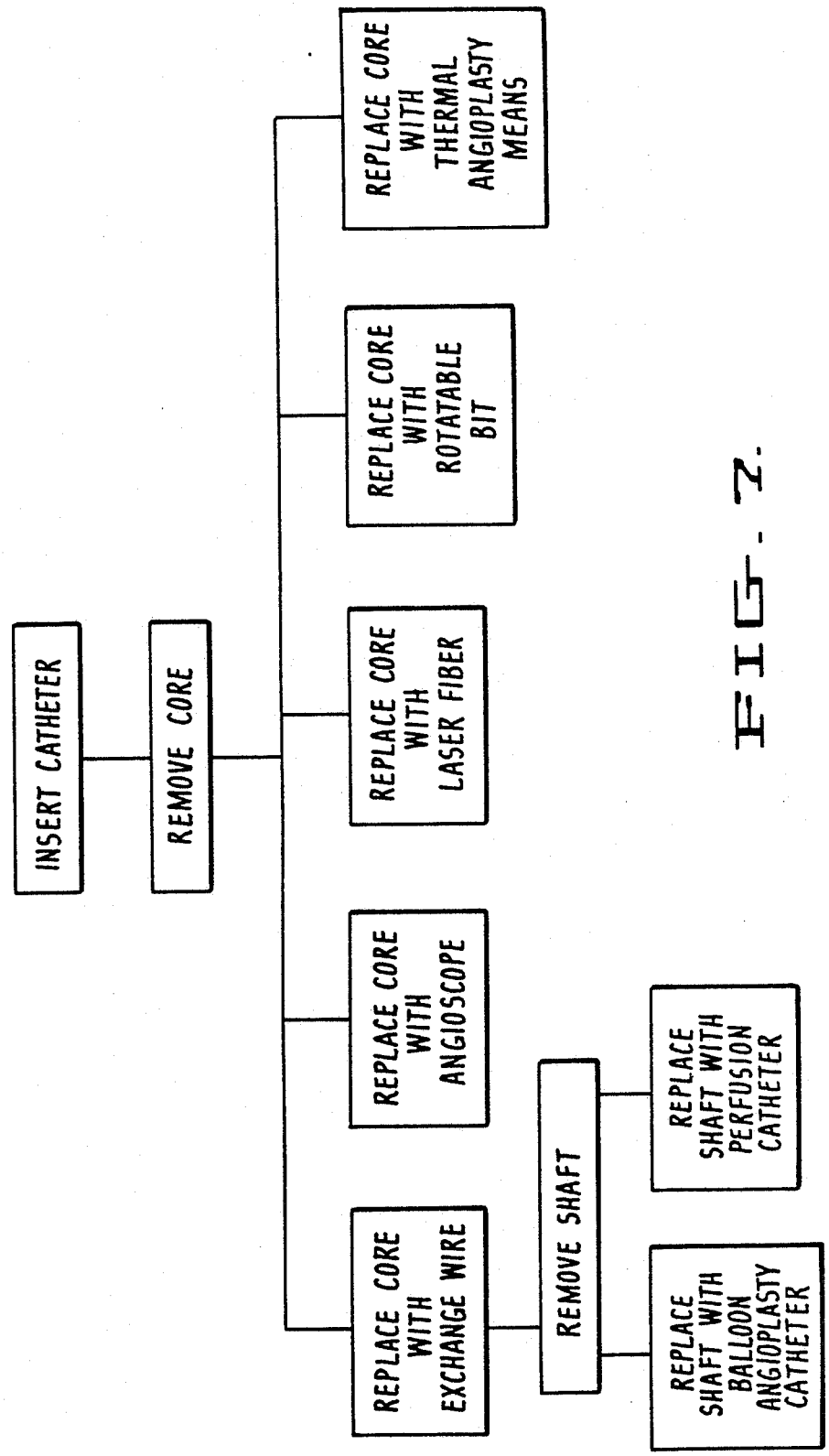

A modification of the shaft of FIG. 1 is illustrated in FIG. 5 and includes a ferrite material 46 provided within shaft 12. Means 48 provides a radio frequency signal to be received by ferrite material 46 using shaft 12 and core 20 as conductors thus heating catheter 10. Alternatively, another modification is illustrated in FIG. 6 and may include the ferrite material 46 impregnated within a portion of inflatable member 34. Similarly, means 48 provides the aforesaid radio frequency signal to be received by ferrite 46.

Figure 4:
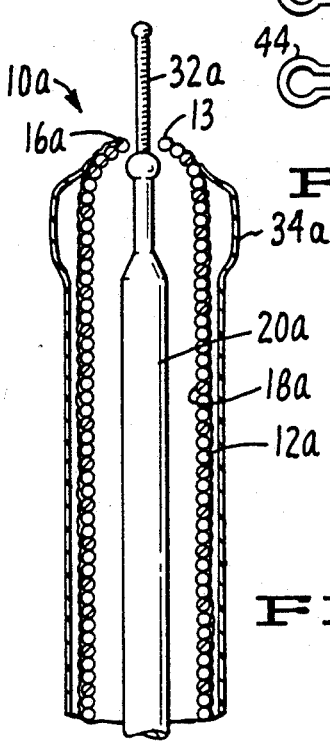
FIG. 4 is a diagrammatic view illustrating another embodiment of this invention.

Another modification of the shaft is illustrated in FIG. 4 wherein shaft 12a includes an aperture 13 formed in second end 16a. Core 20a is also modified in that flexible guidewire 32 is fixedly attached to knob 30a. Balloon 34 and finger loops 42, 44, described above in connection with shaft 12 and core 20 illustrated in FIG. 2, may also be associated with the combination of shaft 12a and core 20a of FIG. 4.

Figure 3:
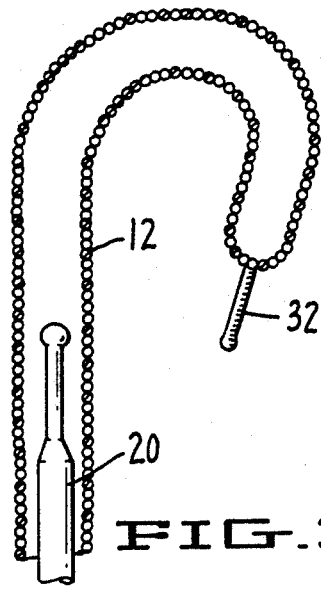
FIG. 3 is another diagrammatic view illustrating the embodiment of FIG. 1 of this invention having the core withdrawn from the shaft.

Catheter 10 is constructed of a spring wire shaft 12 with a movable and removable core 20. This feature is desirable in that it allows variable column strength of shaft 12 and variable flexibility, which is controlled by the operator by either advancing or withdrawing moveable core 20. If stiffness of the shaft is required to "push" through tight lesions, core 20 is advanced and the entire catheter 10 becomes stiffer and has greater "pushability". If extreme flexibility is required, as may be the case in navigating through extremely tortuous vessels, the core 20 of catheter 10 may be withdrawn, see FIG. 3. Core 20 may be withdrawn partially or totally, therefore, increasing the flexibility of catheter 10 from the distal portion to the proximal portion depending on how far back moveable core 20 is withdrawn. Because shaft 12 of catheter 10 is made out of spring wire rather than polymers, shaft 12, even without core 20, has a fair degree of pushability or column strength, yet extreme flexibility. During any given angioplasty procedure, either extreme flexibility or pushability, or both, may be required; therefore, during any procedure, core 20 may be pulled back and advanced according to the desires of the operator. As an additional feature, core 20 may be replaced with a second core of greater or lesser flexibility. Then a "fine-tuning" of column strength is available to the operator.

The unique construction of catheter 10 (FIG. 1), allows for both tip deflection and torquing of leading guidewire 32. Two alternatives are proposed. In the first, the shaft 12 of catheter 10 is closed at the distal end. As core 20 pushes forward and is advanced in contact with closed end 16, catheter 10 is deflected. This deflection is a result of the fact that core 20 is more flexible in portion 28 than in portion 26. This increased flexibility of the distal portion of core 20 as opposed to the proximal portion, is the result of either tapering core 20 so that it is thinner distally than proximally, or creating a joint therein such that an elbow effect is created at the joint and when the catheter is pushed forward, the elbow bends, deflecting the end 24 of core 20 and the end 16 of shaft 12 as well, because shaft 12 is a flexible spring wire. The greater the force applied to core 20, the greater the extent of angulation of catheter 10. The radius of angulation of catheter 10 is controlled by location of the taper or the position of the elbow joint. The closer the elbow joint to end 24, or the less length of taper at end 24, the smaller the radius of angulation and vice versa. Using this criteria, angulation of greater than 120° can be obtained.

The end of the core 20 is blunted by terminal knob 30, so as to avoid perforation of shaft 12 by core 20 as it advances through tortuous regions of the arteries and as it pushes against closed end 16. In FIG. 1, a very flexible guidewire 32 of about 1–7 cm, 0.008 inches to 0.018 inches, may be fixedly connected to end 16 of shaft 12. This "fixed wire" connected to the distal portion of shaft 12, allows the entire catheter 10 to be advanced forward through the arteries with minimal trauma. Guidewire 32 is deflectable by deflecting end 16 of shaft 12 and torquable by torquing shaft 12 of catheter 10.

In FIG. 4, the similar but slightly modified, steerable catheter 10a is presented. In this variation, distal end 16a of shaft 12a is not entirely closed but includes aperture 13. Core 20a is similar to core 20, except that preferably welded to knob 30a is the highly flexible, 1–7 cm, 0.012 inch to 0.025 inch, terminal guidewire 32. In this system, core 20a is withdrawn and advanced for varying the shaft stiffness as explained above. The main difference being that flexible guidewire 32 is connected directly to the core rather than to the shaft. As core 20a is advanced, guidewire 32 is advanced so that it protrudes through aperture 13 in end 16a of shaft 12a. However, at the position of the weld between guidewire 32 and core 20a, the diameter of knob 30a is larger than the diameter of aperture 13. Therefore, in order to deflect catheter 10a, the operator advances core 20a so that knob 30a pushes against the distal end 16a of shaft 12a. In this manner, because of the taper in core 20a, the core is deflected. This deflects shaft 12a of catheter 10a as well as guidewire 32 protruding from end 16a. Further, if the operator requires torque on guidewire 32, he roates the proximal portion of core 20a and the torque is transmitted through core 20a to the distal guidewire 32, thereby torquing the guidewire. This system then allows the operator to have both tp angulation and torquability through an ulra low-profile system with variable shaft flexibility.

Because catheter 10 is constructed with a moveable core 20, when core 20 is removed shaft 12 becomes hollow. In FIG. 4, where there is an aperture 13 in end 16a of shaft 12a, aperture 13 can be used in several settings. If the operator is proceeding with this system and an unexpected closure of the artery results, such that a long exchange wire needs to be inserted so that a "bail out" catheter may be placed, or so that a larger balloon can be inserted, then the operator may remove core 20a of catheter 10a and through the hollow passage 18a of shaft 12a, insert a long exchange wire which will protrude through aperture 13 in end 16a of shaft 12a and, due to the absence of knob 30a, allow shaft 12a to be removed and a larger balloon or "bail-out" catheter to be placed over it. This is a unique feature of this system, in that no other angulating, torquable catheter is able to provide the ability of both a fixed wire and an over-the-wire system in the same catheter.

The new procedures of coronary angioscopy and laser angioplasty may have significant use as adjuncts to balloon angioplasty. The catheter of this invention has significant applicability to both angioscopy and laser angioplasty. If the operator is performing a case with catheter 10a of FIG. 4, and he then decides to perform coronary angioscopy, the following can be undertaken. First, catheter 10a is advanced using the standard technique to the location of interest. Second, core 20a of catheter 10a is withdrawn and the operator then inserts an appropriately-sized, highly-flexible angioscope into the shaft of the catheter and advances it to aperture 13. This system therefore, provides uniquely, the ability to perform coronary angioscopy during balloon angioplasty. By advancing the coronary angioscope through hollow passage 18a, the scope can be advanced without actually coming into contact with the arterial wall. That is, the scope is always closed within the shaft 12a of catheter 10a. This is a significant advance over current methods of coronary angioscopy, which exposes the tip of the scope to the wall of the artery, thereby allowing the potential for abrasion and dissection of the arterial wall. Also, the tip of the angioscope can be quite sharp and therefore protrude through the plastic at regions of bends. Because of the metallic structure of catheter 10a, it does not occur with this system. Flushing of blood may then be performed through the guiding catheter, with or without the balloon inflated, so as to allow the clear field in which to view with the angioscope.

Similarly, if laser angioplasty is performed, the laser fiber connected to virtually any laser source, can be advanced through hollow passage 18a of catheter 10a, up to and protruding through, if necessary, aperture 13. This again allows for advancement of the laser fiber without contact to the arterial wall, minimizing the potential of abrasion. This is not easily performed with conventional polymer catheters, in that the tip of the laser fiber can be quite sharp and therefore protrude through the plastic at regions of bends. Because of the metallic structure of catheter 10a, it does not occur with this system.

Balloon 34a in this balloon angioplasty system is placed directly over shaft 12a. The polymer of which balloon 34a is constructed, is connected and attached or affixed to distal end 16a of shaft 12a. Balloon 34a is somewhat proximal to end 16a and then the polymer extends back to the proximal portion of catheter 10a. The proximal portion of balloon 34a is connected to the balloon inflation apparatus as in FIG. 2. Balloon 34a can be composed of any one of a variety of standard materials (polyethylene, polyvinylchloride) or may be made of new ultra-thin materials, such as the Dupont product PET. Because balloon 34a is placed directly over shaft 12a and because the balloon material can be made very low profile, this catheter has an extremely low profile, only slightly above that of shaft 12a. Shaft 12a can have a variable size depending on what is desired and can range from about 0.014 inch to any upper size desired. Also possible, would be the incorporation of novel polymer technology. In this system, some catheters could be composed of available polymers, strengthened with thin strands of impregnated fibers. This would allow very high burst strengths, in excess of 15 atmospheres, yet not create a high profile. This would allow for high pressure inflations with a very low-profile catheter system.

Because of the extremely low profile, this system may be inserted through conventional, diagnostic catheters rather than the special PTCA guide catheters currently used during all angioplasty procedures. The diagnostic catheters have handling characteristics superior to the PTCA guide catheters, and are also smaller in diameter and less traumatic to the coronary arteries. This therefore, provides a significant advantage over available systems.

Figure 2:
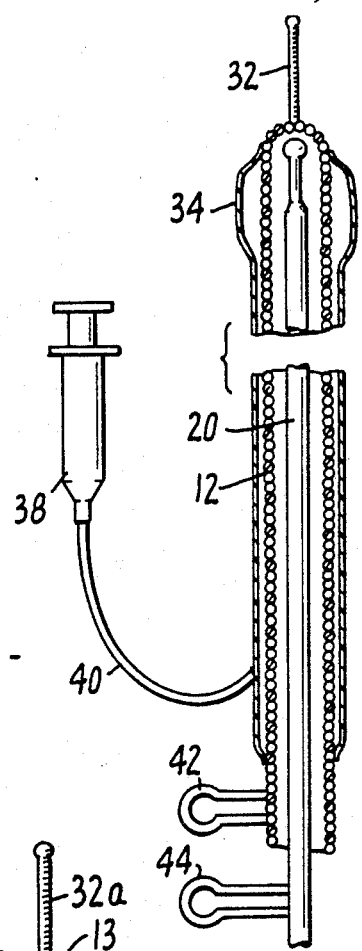
FIG. 2 is another diagrammatic view illustrating the embodiment of FIG. 1 of this invention.

The optionally provided pistol-grip handles provided by loops 42, 44 connected to the proximal portion of shaft 12, 12a and core 20, 20a, allow very fine control of the core and the shaft, using only one hand (FIG. 2). This, therefore, allows for significant advantages over currently available systems. The pistol-grip handles allow for simple advancement of the entire catheter system, or withdrawal, or indiviual advancement or withdrawal of the core and shaft, torque of the shaft, or the core, or both, core advancement or withdrawal for varying shaft flexibility and pushability, and core advancement so that tip angulation can be achieved by the mechanisms described above. This is a significant advantage over currently available systems.

A modified version of catheter 10a could also be useful for balloon valvuloplasty. The modifications would incorporate a larger balloon (3–8 cm in length, 12–25 mm in diameter). Shaft 12a of FIG. 4 would be employed. This would allow tip steerability for retrograde crossing of the aortic valve, (no current valvuloplasty system has steerability), movable core for variable flexibility and column strength, (great flexibility is required for navigating up tortuous, peripheral vessels to reach the valve, yet pushability column strength is required to move across the narrowed valve orifice), once the valve is crossed, the core can be removed to allow pressure monitoring through the hollow shaft, (distal pressure monitoring during valvuloplasty is not possible with conventional systems, and the spring-wire is sufficiently flexible and atraumatic to sit in the ventricle without the core and tip wire) and low profile of the shaft with fiber-strengthened balloon, allows for overall low profile.

Using either of catheter 10 and 10a or virtually any conventional balloon angioplasty catheter, a significant modification can be achieved. There is scientific evidence to support the notion that heating the artery to a temperature greater than some critical temperature, currently thought to be about 70° C., may ameliorate the restenosis found in 25–30g% of patients following balloon angioplasty. Restenosis is considered the single most important problem with balloon angioplasty and any device which could ameliorate this problem would have enormous clinical impact. Several potential solutions to this problem are proposed, all of which are related to methods of heating the balloon. One solution (FIG. 5) involves placement of a small amount of ferrite material 46 at the distal and of core 20 in the balloon portion of catheter 10. This ferrite is a ferromagnetic material which is capable of heating when coupled to an appropriately tuned radiofrequency energy source. Radiofrequency energy in the mega hertz or microwave portion of the electromagnetic spectrum is transmitted down shaft 12 of angioplasty catheter 10 using core 20 and shaft 12 as conducting material. This energy then couples to the ferrite material 46 generating intense localized heating. Heat from ferrite 46 heats the fluid used to expand balloon 34 providing a heated balloon of greater than 70° C. This balloon could be used for coronary or peripheral arterial inflation and by virtue of the temperature achieved is capable of killing smooth muscle cells in the wall of the artery. It is then smooth muscle cells which are responsible for restenosis following angioplasty and it is claimed that the thermal energy from the balloon catheter would therefore kill the progenitor cells responsible for restenosis. Another solution (FIG. 6) involves the impregnation of the balloon material itself with the ferromagnetic material 46. The radiofrequency energy is then delivered from outside the body and coupled into the ferromagnetic material 46 in balloon 34. That is, the ferromagnetic material in balloon 34 acts as an antenna for the radiofrequency energy. This generates intense heating of balloon 34 to greater than 70° C. and kills the smooth muscle cells thereby preventing restenosis. Other suitable means of heating a balloon will yield equally effective results.

Above-described is a system for producing a small central lumen in a totally occluded artery which could then be followed by balloon angioplasty. If an artery is totally occluded then it is difficult to place the balloon into the occlusion so that inflation can commence. It is proposed that the above-described catheter 10a could be used to solve this problem. Catheter 10a could be advanced to the blockage. Core 20a can be removed leaving behind the hollow shaft 12a. Through passage 10a in shaft 12a, can be placed a specially fabricated wire which protrudes through aperture 13. The proximal portion of the new central wire is connected to a rotating bit which is powered by either batteries or standard electric current. The rotating bit rotates from about 10,000 to about 250,000 rpm thereby causing the central wire to rotate at the same frequency. This rotating wire will act as a drill and burrow a small central channel through the totally occluded artery. Once this has occurred the catheter is advanced through the blockage such that now the balloon is placed within the blockage and is capable of dilating it. This procedure has application for sequential recanalization and balloon dilation of totally occluded arteries.

What is claimed is:

1. A catheter for balloon angioplasty comprising:
    a flexible shaft having a hollow passage therein, said flexible shaft having a first proximal end which is open and a second distal end which is closed;
    a core means movably and removably mounted within said passage, said core means having a first proximal end and a second distal end, said ends adjacent with first and second ends of said flexible shaft, respectively, said core means having a first flexible portion extending along its length from said first proximal end and a second flexible portion being of greater flexibility than said first flexible portion, said second flexible portion extending to said second distal end, said core means having an enlarged terminal knob at said second distal end thereof, said knob contacting said second distal end of said flexible shaft upon axial movement of said core means, further axial movement of said core means causing bending and buckling of said second flexible portion of said core means in turn bending said flexible shaft and causing angulation of said second distal end of said flexible shaft;
    a flexible guide wire externally attached to the second distal end of said flexible shaft, said flexible guide wire axially extending away from said second distal end; and
    an inflatable member having a non-inflatable sheath covering an external surface of said flexible shaft near the second distal end of said flexible shaft and further including means for inflating said inflatable member.

2. A catheter as in claim 1 further including ferrite material within said flexible shaft near said second distal end of said flexible shaft and including means for transmitting radio frequency energy through said flexible shaft to said ferrite material to cause heating of said ferrite material to heat said second distal end of said flexible shaft.

3. A catheter for balloon angioplasty comprising:
    a flexible shaft having a hollow passage therein, said flexible shaft having a first proximal end which is open and a second distal end which is partially open having a reduced cross-section;
    a core means movably and removably mounted within said passage, said core means having a first proximal end and a second distal end, said ends adjacent said first and second ends of said flexible shaft, respectively, said core means having a first flexible portion extending along its length from said first proximal end and a second flexible portion being of greater flexibility than said first flexible portion, said second flexible portion extending to said second proximal end, said core means having an enlarged terminal knob at said second distal end thereof, said knob contcting said reduced cross-section of said second distal end of said flexible shaft upon axial movement of said core means, further axial movement of said core means causing bending and buckling of said second flexible portion of said core means bending said flexible shaft and causing angulation of said second distal end of said flexible shaft;
    a flexible guide wire attached to said terminal knob and axially extending away from said knob, said guide wire axially extensible through the opening in said second distal end of said flexible shaft; and
    an inflatable member having a non-inflatable sheath covering an external surface of said flexible shaft near the second distal end of said flexible shaft and further including means for inflating said inflatable member.

4. A catheter as in claim 3 further including ferrite material within said flexible shaft near said second distal end of said flexible shaft and including means for transmitting radio frequency energy through said flexible shaft to said ferrite material to cause heating of said ferrite material to heat said second distal end of said flexible shaft.

5. A method of performing a combined fixed wire and movable wire angioplasty including the steps of:
    (a) inserting a catheter in a vascular tree, said catheter including a flexible shaft having a hollow passage therein, said flexible shaft having a first proximal end which is open and a second distal end which is partially open having a reduced cross-section, said catheter including a core means movably and removably mounted within said passage, said core means having a first proximal end and a second distal end, said ends adjacent said first and second ends of said flexible shaft, respectively, said core means having a first flexible portion extending along its length from said first proximal end and a second flexible portion being of greater flexibility than said first flexible portion, said second flexible portion extending to said second proximal end, said core means having an enlarged terminal knob at said second distal end thereof, said knob contacting said reduced cross-section of said second distal end of said flexible shaft upon axial movement of said core means, said catheter including a flexible guide wire attached to said terminal knob and axially extending away from said knob, said guide wire axially extensible through the opening in said second distal end of said flexible shaft, said guide wire further including an inflatable member having a non-inflatable sheath covering an external surface of said flexible shaft near said second distal end of said flexible shaft and further including means for inflating said inflatable member; and (b) moving said core means axially toward and into contact with said reduced cross-section causing bending and buckling of said second flexible portion of said core means bending said flexible shaft and causing angulation of said second distal end of said flexible shaft.

6. A method according to claim 5 further including the steps of:
(c) removing said core means through said first proximal end of said flexible shaft;
(d) inserting an exchange wire within said flexible shaft;
(e) removing said flexible shaft; and
(f) inserting a different balloon angioplasty catheter over said exchange wire.

7. A method according to claim 5 further including the steps of:
(c) removing said core means through said first proximal end of said flexible shaft;
(d) inserting an exchange wire within said flexible shaft;
(e) removing said flexible shaft; and
(f) inserting a perfusion catheter over said exchange wire.

8. A method according to claim 5 further including the steps of:
(c) removing said core means through said first proximal end of said flexible shaft; and
(d) inserting an angioscope within said flexible shaft.

9. A method according to claim 5 further including the steps of:
(c) removing said core means through said first proximal end of said flexible shaft; and
(d) inserting a laser fiber within said flexible shaft.

10. A method according to claim 5 further including the steps of:
(c) removing said core means through said first proximal end of said flexible shaft; and
(d) inserting a rotatable bit within said flexible shaft.

11. A method according to claim 5 further including the steps of:
(c) removing said core means through said first proximal end of said flexible shaft; and
(d) inserting within said flexible shaft a thermal angioplasty means for thermal oblation and remodeling of tissue.

12. A kit including:
a catheter having a flexible shaft having a hollow passage therein, said flexible shaft having a first proximal end which is open and a second distal end which is partially open having a reduced cross-section, said catheter including a core means movably and removably mounted within said passage, said core means having a first proximal end and a second distal end, said ends adjacent said first and second ends of said flexible shaft, respectively, said core means having a first flexible portion extending along its length from said first proximal end and a second flexible portion being of greater flexibility than said first flexible portion, said second flexible portion extending to said second proximal end, said core means having an enlarged terminal knob at said second distal end thereof, said knob contacting said reduced cross-section of said second distal end of said flexible shaft upon axial movement of said core means, further axial movement of said core means causing bending and buckling of said core means, in turn bending said flexible shaft and causing angulation of said second distal end of said flexible shaft, said catheter further including a flexible guide wire attached to said terminal knob and axially extending away from said knob, said guide wire axially extensible through the opening in said second distal end of said flexible shaft, said catheter further including an inflatable member having a noninflatable sheath covering an external surface of said flexible shaft near the second distal end of said flexible shaft and further including means for inflating said inflatable member;
components in the form of an exchange wire, an angioscope, a laser fiber, a rotatable bit, and a thermal angioplasty means for thermal oblation and remodeling of tissue, all of said components sized to be insertable within said flexible shaft upon removal of said core means; and
a different balloon angioplasty catheter and a perfusion catheter, said balloon angioplasty catheter and said perfusion catheter sized to be inserted over said exchange wire.

* * * * *

UNITED STATES PATENT AND TRADEMARK OFFICE
CERTIFICATE OF CORRECTION

PATENT NO. : 4,808,164

DATED : February 28, 1989

INVENTOR(S) : Robert Hess

It is certified that error appears in the above-identified patent and that said Letters Patent is hereby corrected as shown below:

Column 2, line 67, delete "A" and insert --An--.

Column 4, line 25, delete "above. The" and insert --above, the--.

Column 4, line 39, delete "roates" and insert --rotates--.

Column 4, line 42, delete "tp" and insert --tip--.

Column 4, line 43, delete "ulra" and insert --ultra--.

Column 6, line 10, delete "indiviual" and insert --individual--.

Column 6, line 42, delete "25-30g%" and insert -- 25-30% --.

Column 6, line 50, delete "and" and insert --end--.

Column 8, line 21, delete "contcting" and insert --contacting--.

Column 10, line 35, delete "noninflatable" and insert -- non-inflatable --.

Signed and Sealed this

Third Day of April, 1990

*Attest:*

HARRY F. MANBECK, JR.

*Attesting Officer*   *Commissioner of Patents and Trademarks*